United States Patent
Shi et al.

(10) Patent No.: US 10,426,402 B2
(45) Date of Patent: Oct. 1, 2019

(54) SKIN PROXIMITY AND TILT EFFECT SENSOR

(71) Applicant: Apple Inc., Cupertino, CA (US)

(72) Inventors: Justin Shi, Sunnyvale, CA (US); Brian R. Land, Woodside, CA (US); Nevzat Akin Kestelli, San Jose, CA (US); Serhan O. Isikman, Sunnyvale, CA (US)

(73) Assignee: APPLE INC., Cupertino, CA (US)

( * ) Notice: Subject to any disclaimer, the term of this patent is extended or adjusted under 35 U.S.C. 154(b) by 474 days.

(21) Appl. No.: 15/100,627

(22) PCT Filed: Dec. 20, 2013

(86) PCT No.: PCT/US2013/077319
§ 371 (c)(1),
(2) Date: May 31, 2016

(87) PCT Pub. No.: WO2015/094378
PCT Pub. Date: Jun. 25, 2015

(65) Prior Publication Data
US 2016/0296172 A1 Oct. 13, 2016

(51) Int. Cl.
*A61B 5/00* (2006.01)
*A61B 5/11* (2006.01)
*A61B 5/024* (2006.01)

(52) U.S. Cl.
CPC .......... *A61B 5/6844* (2013.01); *A61B 5/0059* (2013.01); *A61B 5/02416* (2013.01);
(Continued)

(58) Field of Classification Search
CPC ... A61B 5/1118; A61B 5/1121; A61B 5/0059; A61B 5/0075; A61B 5/02416; A61B 5/6844
See application file for complete search history.

(56) References Cited

U.S. PATENT DOCUMENTS 5,483,261 A 1/1996 Yasutake
5,488,204 A 1/1996 Mead et al.
(Continued)

FOREIGN PATENT DOCUMENTS

CN 203057245 U 7/2013
CN 103376971 A 10/2013
(Continued)

OTHER PUBLICATIONS

Lee, S.K. et al. (Apr. 1985). "A Multi-Touch Three Dimensional Touch-Sensitive Tablet," *Proceedings of CHI: ACM Conference on Human Factors in Computing Systems*, pp. 21-25.
(Continued)

*Primary Examiner* — Max F Hindenburg
(74) *Attorney, Agent, or Firm* — Morrison & Foerster LLP

(57) ABSTRACT

A portable electronic device include one or more electrodes for calculating distances and rotational angles between the device and the user is disclosed. Based on the calculated distances and rotational angles, a physical activity of the user can be determined. Additionally, the calculated distances and rotational angles can be used for compensation of optical artifacts in one or more signals detected by the device. User movement or physical activity can introduce optical artifacts, which can lead to erroneous determination of the one or more characteristics. The calculated distances and rotational angles can be used to reduce or remove the optical artifacts, leading to a more accurate determination of the one or more characteristics of the user.

11 Claims, 17 Drawing Sheets

(52) U.S. Cl.
CPC .......... *A61B 5/1118* (2013.01); *A61B 5/6898* (2013.01); *A61B 5/721* (2013.01); *A61B 5/7278* (2013.01); *A61B 5/742* (2013.01); *A61B 5/7475* (2013.01); *A61B 2560/0468* (2013.01); *A61B 2562/046* (2013.01); *A61B 2562/14* (2013.01)

(56) References Cited

U.S. PATENT DOCUMENTS

| | | |
|---|---|---|
| 5,825,352 A | 10/1998 | Bisset et al. |
| 5,835,079 A | 11/1998 | Shieh |
| 5,880,411 A | 3/1999 | Gillespie et al. |
| 6,188,391 B1 | 2/2001 | Seely et al. |
| 6,310,610 B1 | 10/2001 | Beaton et al. |
| 6,323,846 B1 | 11/2001 | Westerman et al. |
| 6,690,387 B2 | 2/2004 | Zimmerman et al. |
| 7,015,894 B2 | 3/2006 | Morohoshi |
| 7,184,064 B2 | 2/2007 | Zimmerman et al. |
| 7,616,110 B2 | 11/2009 | Crump et al. |
| 7,663,607 B2 | 2/2010 | Hotelling et al. |
| 8,378,811 B2 | 2/2013 | Crump et al. |
| 8,479,122 B2 | 7/2013 | Hotelling et al. |
| 8,618,930 B2 | 12/2013 | Papadopoulos et al. |
| 8,914,088 B2 * | 12/2014 | Buice .................. A61B 5/14551 600/310 |
| 9,118,330 B2 * | 8/2015 | Beyly ..................... G06F 3/044 |
| 9,877,669 B2 * | 1/2018 | Gallagher ............ A61B 5/6838 |
| 2006/0197753 A1 | 9/2006 | Hotelling |
| 2014/0155705 A1 | 6/2014 | Papadopoulos et al. |
| 2015/0002455 A1 | 1/2015 | Zhang et al. |

FOREIGN PATENT DOCUMENTS

| | | |
|---|---|---|
| JP | 2000-163031 A | 6/2000 |
| JP | 2002-342033 A | 11/2002 |
| WO | WO-2010/140106 A1 | 12/2010 |
| WO | WO-2013/184375 A1 | 12/2013 |

OTHER PUBLICATIONS

Rubine, D.H. (Dec. 1991). "The Automatic Recognition of Gestures," CMU-CS-91-202, Submitted in Partial Fulfillment of the Requirements for the Degree of Doctor of Philosophy in Computer Science at Carnegie Mellon University, 285 pages.

Rubine, D.H. (May 1992). "Combining Gestures and Direct Manipulation," CHI '92, pp. 659-660.

Westerman, W. (Spring 1999). "Hand Tracking, Finger Identification, and Chordic Manipulation on a Multi-Touch Surface," A Dissertation Submitted to the Faculty of the University of Delaware in Partial Fulfillment of the Requirements for the Degree of Doctor of Philosophy in Electrical Engineering, 364 pages.

* cited by examiner

US 10,426,402 B2

SKIN PROXIMITY AND TILT EFFECT SENSOR

CROSS-REFERENCE TO RELATED APPLICATION

This application is a National Phase application under 35 U.S.C. § 371 of International Application No. PCT/US2013/077319, filed Dec. 20, 2013, the content of which is hereby incorporated by reference in its entirety for all intended purposes.

FIELD OF THE DISCLOSURE

This is related generally to the determination of distances and rotational angles of a portable electronic device relative to a user's body part, and more specifically to determination of skin proximity and tilt effect through the underside of the device.

BACKGROUND OF THE DISCLOSURE

Some conventional portable electronic devices can be worn or otherwise attached to a user and provide functionality related to the physical activity of a user. For example, many conventional wearable devices can monitor the heart rate of a user. However, conventional devices are limited in their functionality, and their accuracy can be limited by changes in the distance of the user with respect to the wearable device.

SUMMARY OF THE DISCLOSURE

The following disclosure includes examples of determining a proximity and rotational angles of a user relative to a portable electronic device. The portable electronic device can be worn or resting on a user body part, or attached to a user body part. The device can include electrodes for calculating distances and rotational angles between the user body part and the device. Based on the calculated distances and rotational angles, a physical activity of the user can be determined. Additionally, the calculated distances and rotational angles can be used for compensation of optical artifacts in one or more signals detected or generated by the device. For example, the device can include one or more light emitters and sensors for determining or at least estimating or predicting one or more characteristics of the user, such as a physical activity of the user. User movement or physical activity can introduce optical artifacts, which can lead to erroneous determination of the one or more characteristics. The calculated distances and rotational angles can be used to reduce or remove the optical artifacts, leading to a more accurate determination of the one or more characteristics of the user.

DETAILED DESCRIPTION

In the following description of examples, reference is made to the accompanying drawings which form a part hereof, and in which it is shown by way of illustration specific examples that can be practiced. It is to be understood that other examples can be used and structural changes can be made without departing from the scope of the disclosed examples.

A portable electronic device may be worn or resting on a user body part, or attached to a user body part. Distances and rotational angles between the device and the user can be calculated using electrodes on the device. Based on the calculated distances and rotational angles, a physical activity of the user can be determined. Additionally, the calculated distances and rotational angles can be used for compensation of optical artifacts in one or more signals detected by the device. For example, the device can include one or more light emitters and sensors for determining one or more characteristics of the user. User movement or physical activity can introduce optical artifacts, which can lead to erroneous determination of the one or more characteristics. The calculated distances and rotational angles can be used to reduce or remove the optical artifacts, leading to a more accurate determination of the one or more characteristics of the user.

Figure 1:
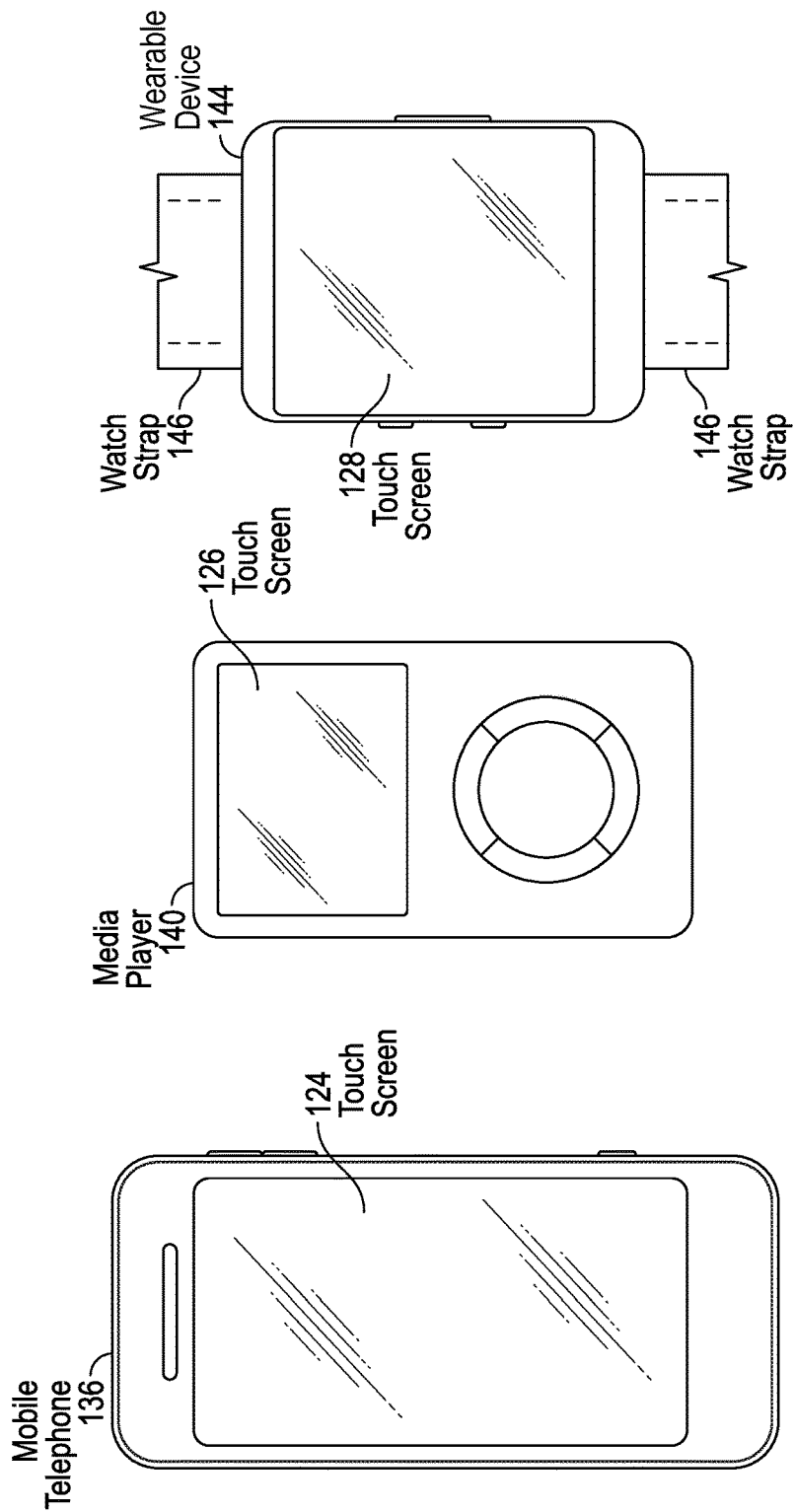
FIGS. 1A-1C illustrate exemplary portable electronic devices in which examples of the disclosure may be implemented.

FIGS. 1A-1C illustrate exemplary portable electronic devices in which examples of the disclosure may be implemented. FIG. 1A illustrates an exemplary mobile telephone 136 that includes a touch screen 124. Touch screen 124 can include a touch panel portion for touch detection, and a display portion for displaying images on the touch screen. As used throughout this disclosure, "touch screen" can refer to the touch panel portion for touch or hover detection, the display portion of the touch screen, or both. FIG. 1B illustrates an exemplary digital media player 140 that includes touch screen 126. FIG. 1C illustrates an exemplary wearable device 144 that includes touch screen 128. Touch screens 124, 126, and 128 may be based on, for example, self-capacitance or mutual capacitance, or another touch sensing technology. For example, in a self-capacitance based touch system, an individual electrode with a self-capacitance to ground can be used to form a touch pixel (touch node) for detecting touch. As an object approaches the touch pixel, an additional capacitance to ground can be formed between the object and the touch pixel. The additional capacitance to ground can result in a net increase in the self-capacitance seen by the touch pixel. This increase in self-capacitance can be detected and measured by a touch sensing system to determine the positions of the one or more objects when they touch the touch screen. A mutual capacitance based touch system can include, for example, drive regions and sense regions, such as drive lines and sense lines. For example, drive lines can be formed in rows while sense lines can be formed in columns (i.e., drive lines and sense lines can be orthogonal). Touch pixels (touch nodes) can be formed at the intersections or adjacencies (in single layer configurations) of the rows and columns. During operation, the rows can be stimulated with an AC waveform and a mutual capacitance can be formed between the row and the column of the touch pixel. As an object approaches the touch pixel, some of the charge coupled between the row and column of the touch pixel can instead be coupled onto the object. This reduction in charge coupling across the touch pixel can result in a net decrease in the mutual capacitance between the row and the column and a reduction in the AC waveform being coupled across the touch pixel. A reduction in the charge-coupled AC waveform can be detected and measured by the touch sensing system to determine the positions of one or more objects when they touch the touch screen. In some examples, a touch screen can be multi-touch, single touch, projection scan, full-imaging multi-touch, or any capacitive touch. The display portions of the touch screens 124, 126, and 128 may be based on display types such as liquid crystal displays (LCD), electroluminescent displays (ELD), field emission displays (FED), light-emitting diode displays (LED), organic light-emitting diode displays (OLED), or quantum dot displays (QLED). Many other types of display technologies can also be used in touch screens 124, 126, and 128, and are equally within the scope of this disclosure.

Figure 2:
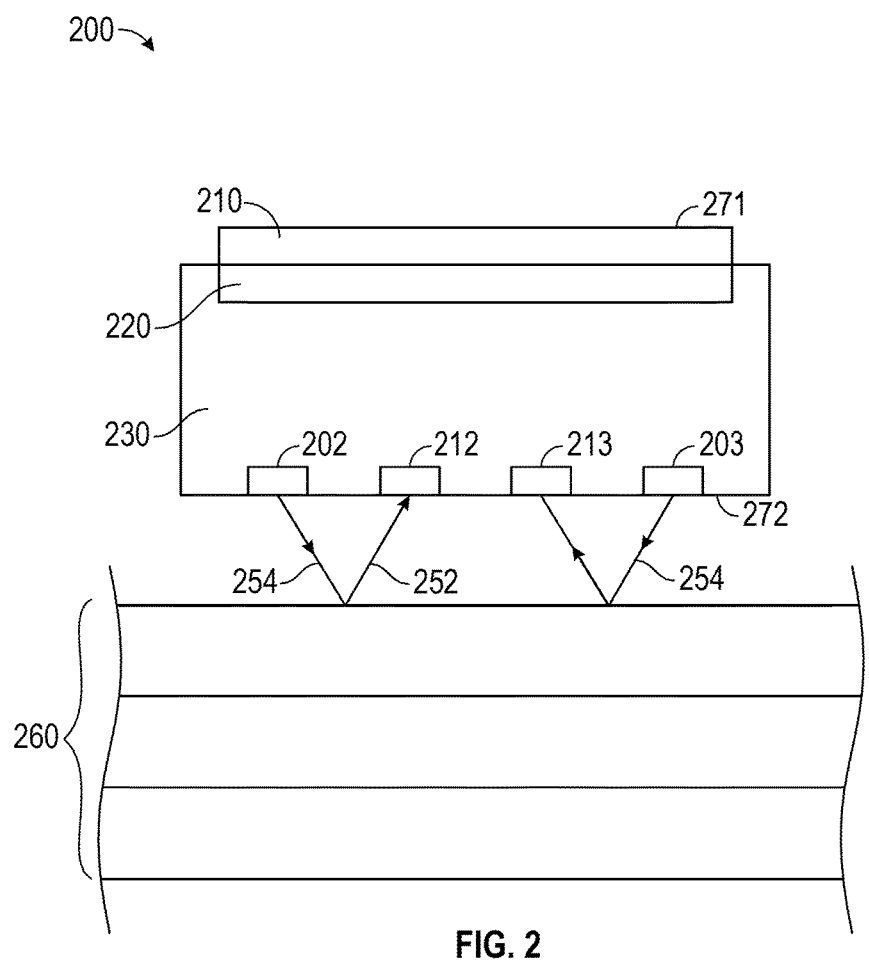
FIG. 2 illustrates a cross-sectional view of an exemplary portable electronic device with light emitters and optical sensors located on the underside of the device.

FIG. 2 illustrates a cross-sectional view of an exemplary portable electronic device with light emitters and optical sensors located on the underside of the device. Exemplary portable electronic device 200 can include a touch screen 210, a display 220, and device body 230. The device 200 can include a top surface 271, which can be, for example, the surface of the touch screen 210 located in a user's line of sight. The device body 230 can include components such as microprocessor chips, printed circuit boards, memory chips, batteries, indicators, and input mechanisms. The device 200 can be attached to, resting on, or touching a part of the user such that the underside 272 of the device faces a body part 260 of the user. While FIG. 2 illustrates top surface 271 located on the surface of the touch screen, top surface 271 can include, and is not limited to, any surface along the same plane as the surface of the touch screen that may or may not detect a touch. Additionally, while FIG. 2 illustrates a portable electronic device with a touch screen and a display as separate components, examples of the disclosure can include, and are not limited to, devices with integrated touch and display panels.

Portable electronic device 200 can include optical devices located on the underside 272. Optical devices can include light emitters 202 and 203, and optical sensors 212 and 213 that can be used, for example, in pairs to determine one or more characteristics of the user. Each light emitter 202 and 203 can emit light 254 towards the body part 260. The human anatomy can allow a portion of the light to absorbed by the skin, flesh, blood, and/or other parts of the user's body, and an additional portion of light can be reflected to optical sensors 212 and 213. The optical sensors 212 and 213 may generate information indicative of one or more characteristics of the reflected light 252 relative to the emitted light 254. Such information can be used to determine information such as heart rate or identification of the user. The signal detected by the optical sensors can be a voltage, a current, or any other signal that can convey information to the device. In some examples, the portable electronic device can include another semiconductor diode or electrical device, configured to convert the light detected by an optical sensor to a measurable current or voltage. In some examples, light emitters 202 and 203 can be different types of light sources and/or emit at different wavelengths, and optical sensors 212 and 213 can absorb the different wavelengths. In some examples, optical sensors can be the same type of sensors, but utilize different filters to absorb different wavelengths. In some examples, light emitters 202 and 203 can be the same type of light sources and/or emit at the same wavelengths, and signals detected by the optical sensors 212 and 213 can be averaged. In some examples, the number of optical sensors can differ from the number of light emitters.

Figure 3A:
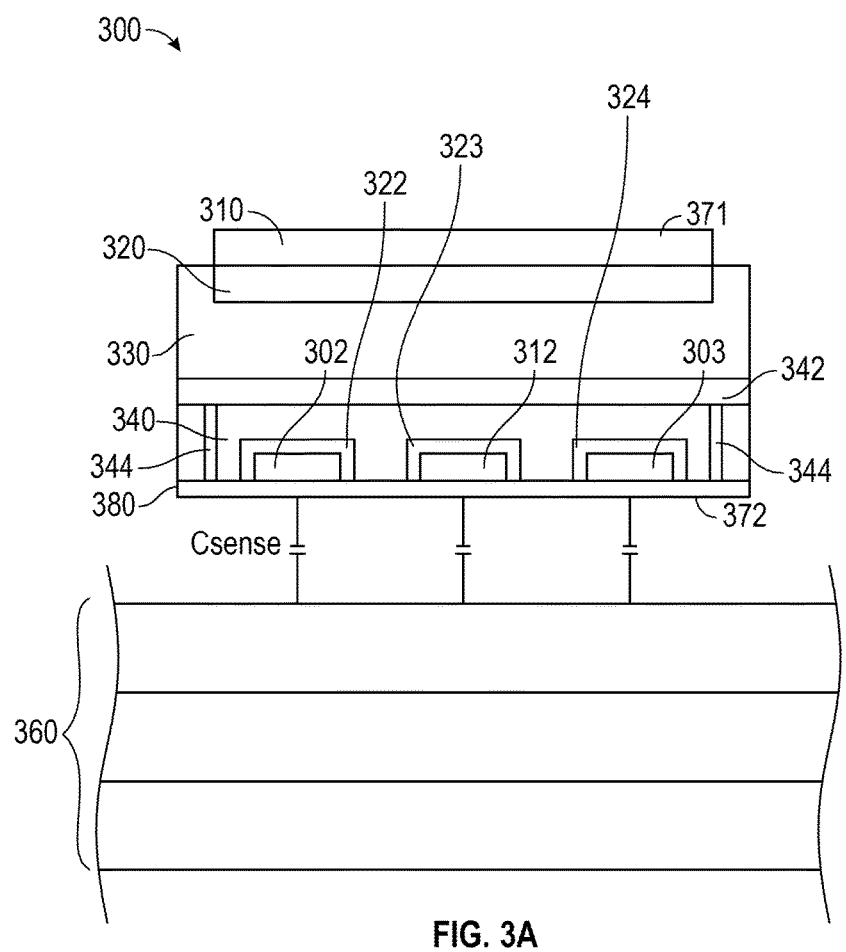
FIGS. 3A-3B illustrate a cross-sectional view and a view of the underside of an exemplary portable electronic device with light emitters, optical sensors, and electrodes located on the underside of the device.
Figure 3B:
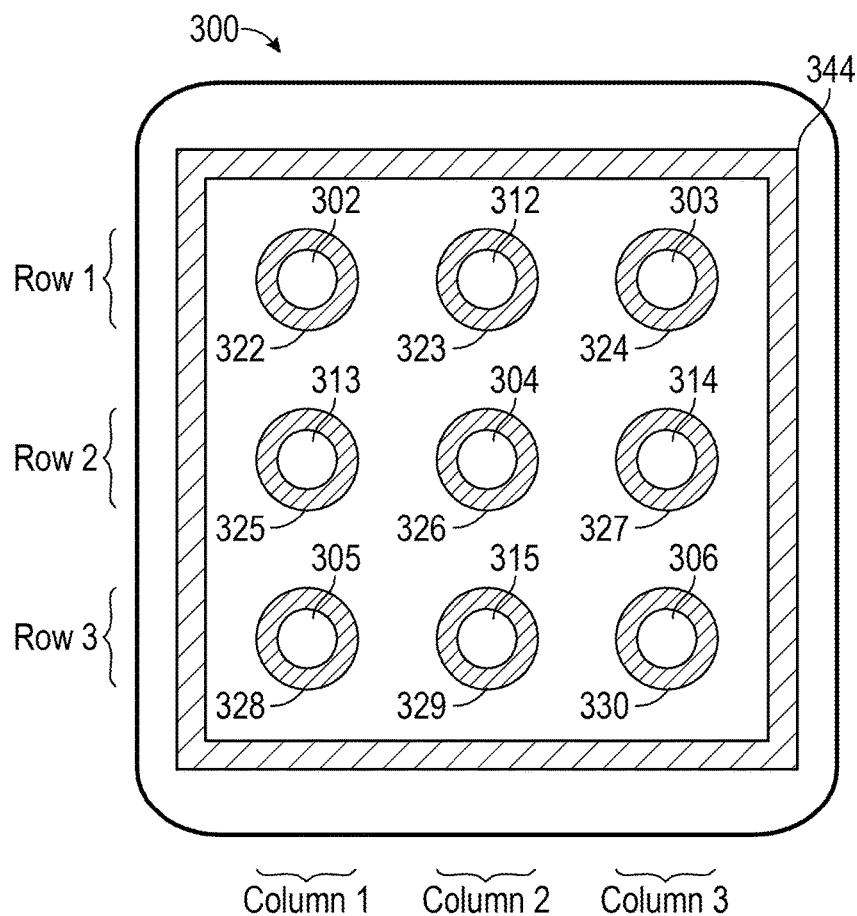

FIG. 3A illustrates a cross-sectional view and FIG. 3B illustrates a view of the underside of an exemplary portable electronic device with light emitters, optical sensors, and electrodes located on the underside of the device. Exemplary portable electronic device 300 can include a touch screen 310, a display 320, and device body 330. The device 300 can include a top surface 371, which can be, for example, the surface of the touch screen 310 located in the user's line of sight. The device body 330 can include components such as microprocessor chips, printed circuit boards, memory chips, batteries, indicators, and input mechanisms. The device 300 can be attached to, resting on, or touching a part of the user such that the underside 372 of the device faces a body part 360 of the user.

Portable electronic device 300 can include optical devices. Optical devices can include light emitters 302-306, optical sensors 312-315, and a plurality of electrodes 322-330. Electrodes 322-330 can be any type of conductive material, such as copper. In some examples, electrodes 32-330 are located on the same layer as the optical devices. In some examples, electrodes 332-330 are located on a different layer than the optical devices. Due to the conductive nature of the human skin, a capacitance can form between the electrodes and the human body part. Some or all of the electrodes can read a capacitance value Csense, and the value of Csense can differ based on the distance of the body part to the device. The device 300 can read Csense and calculate a distance from the user's body part to the electrodes. Based on the calculated distance of the device from the user's skin, the angle of rotation of the device relative to the human body part can also be calculated.

In some examples, some of electrodes 322-330 can be driven by a stimulation signal from a drive circuit to form fringing electric field lines with a neighboring sense electrode. In some examples, those drive electrodes can be stimulated with an AC waveform. A mutual capacitance can form between the driven electrode and another electrode acting as a sense electrode. The human body part can block some of the electric field lines and thus affect the charge coupled onto the sense electrode. Instead of the charge predominantly coupling onto the sense electrode, some of the charge can be coupled to ground through the human body part. This reduction in charge coupling between the drive and sense electrodes can result in a net decrease in capacitance and a reduction in the coupled AC waveform. Based on the change in capacitance ACsense, the distance between the underside of the device and skin can be calculated.

The device 300 can include a cover layer 380 disposed between the electrodes 322-330 and the human body part 360. Cover layer 380 can be used to electrically isolate the skin from the electrodes and to protect the electrodes from damage or corrosion. In some examples, the cover layer can be black to help remove any optical interference. Additionally, an insulating layer 340 and a shield 342 can be disposed above the electrodes away from the user to prevent interaction between the electrodes and the touch screen 310. Additionally or alternatively, device 300 can include a driven shield 344 to prevent external interference. In some examples, driven shield 344 can extend down closer to the human body part 360 than the cover layer 380. In some examples, driven shield 344 can be incorporated into a wristband or strap (such as strap 146 shown in FIG. 1C) attached to the device 300. One or more driven shields can be disposed around one or more electrodes to prevent internal interference, external interference, or both.

Figure 3C:
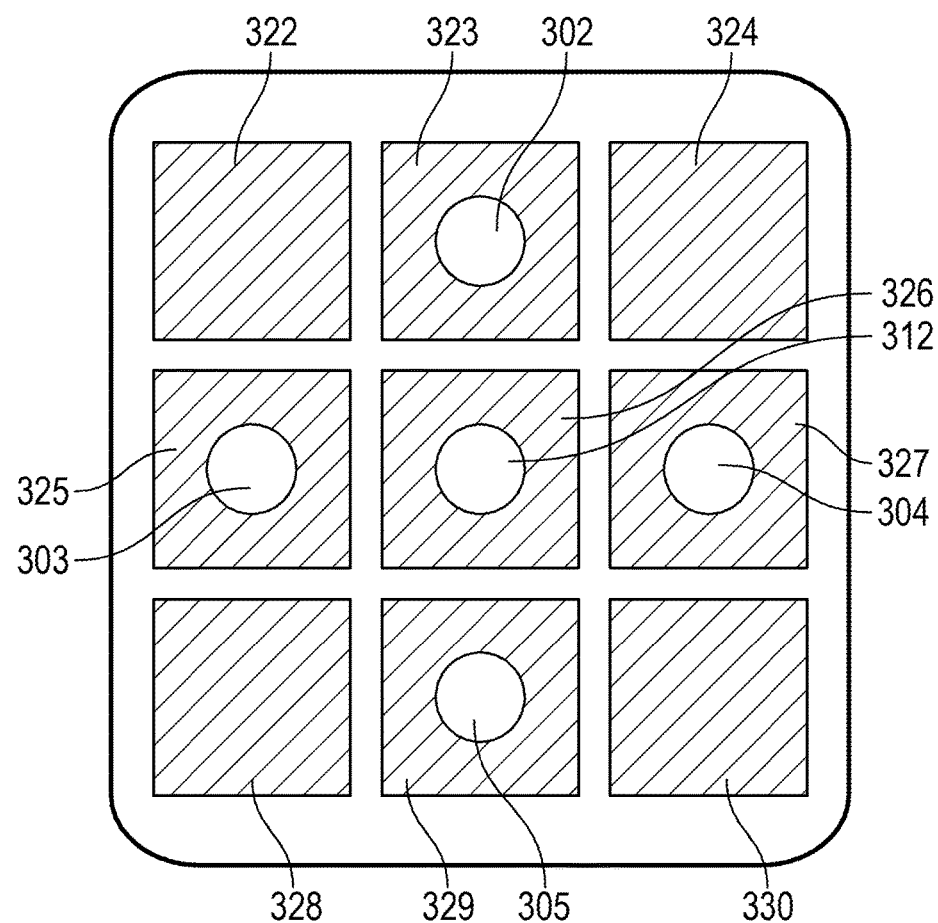
FIG. 3C illustrates a view of the underside of an exemplary portable electronic device with electrodes that substantially fill the entire area of the underside of the device.

In some examples, the electrodes can substantially occupy the underside of the device, as shown in FIG. 3C. Electrodes 322-330 can be separated by a gap. The gap between the electrodes can be sufficient to electrically isolate the electrodes, while allowing the electrodes to substantially fill the area of the underside. Larger electrodes can be used for more sensitive Csense measurements. It is to be understood that the electrodes and optical devices can be any size and can include any type of shape, such as a circle, square, and rectangle. In some examples, the underside of the device may or may not include light emitters and sensors.

Figure 3D:
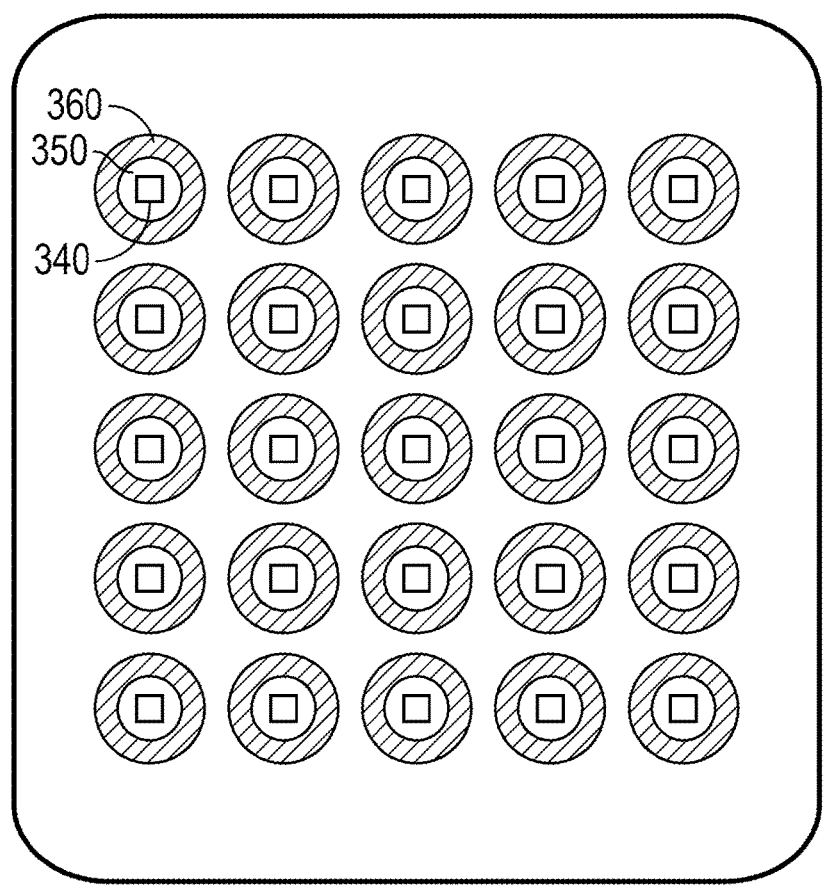
FIG. 3D illustrates a view of the underside of an exemplary portable electronic device comprising multi-row, multi-column skin proximity and tilt effect sensors without a surrounding shield.
Figure 3E:
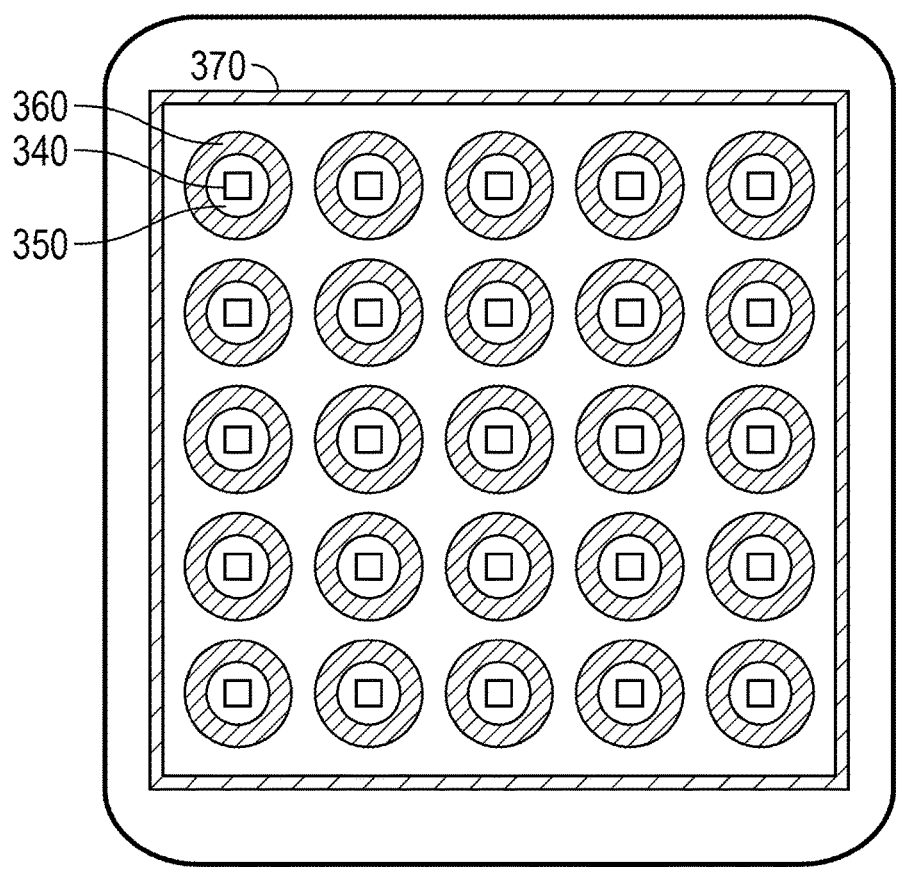
FIG. 3E illustrates a view of the underside of an exemplary portable electronic device comprising multi-row, multi-column skin proximity and tilt effects sensors with a surrounding shield.

FIG. 3D illustrates a view of the underside of an exemplary portable electronic device comprising multi-row, multi-column skin proximity and tilt effect sensors without a surrounding shield. The underside of the device can comprise a plurality of components 340 and 360. Components 340 can be, for example, one or more optical emitters, one or more light sensors, and/or other types of sensors. Optical emitters, light sensors, and other sensors can be used to determine information or detect characteristics of a user. Components 360 can be, for example, electrodes that can be used to form a capacitance between the electrodes and the human body part. Alternatively and/or additionally, fringing electric field lines can form between one or more electrodes driven by a stimulation signal and one or more neighboring sense electrodes. The underside of the device can further comprise a region 350. The region 350 can be unoccupied space or can include a dummy region. Additionally, region 350 can be occupied with another component, such as a second sensor, emitter, or electrode that can be electrically isolated from components 340 and 360. FIG. 3E illustrates a view of the underside of an exemplary portable electronic device comprising multi-row, multi-column skin proximity and tilt effect sensors with a surrounding shield. The surrounding shield 370 can be used to prevent internal and/or external interference. While FIGS. 3D-3E illustrate multi-row, multi-column sensors, examples of the disclosure are not limited to the number of sensors shown in the figure.

Additionally, examples of the disclosure are not limited to the shapes and configuration of the components 340 and 360 and region 350. In some examples, components 340 can include electrodes and components 360 can include optical emitters and light sensors. In some examples, components 340 and 360 can include any combination of one or more electrodes, one of more optical emitters, one or more light sensors, and one or more other types of sensors, and are not limited to one type of component.

Figure 4A:
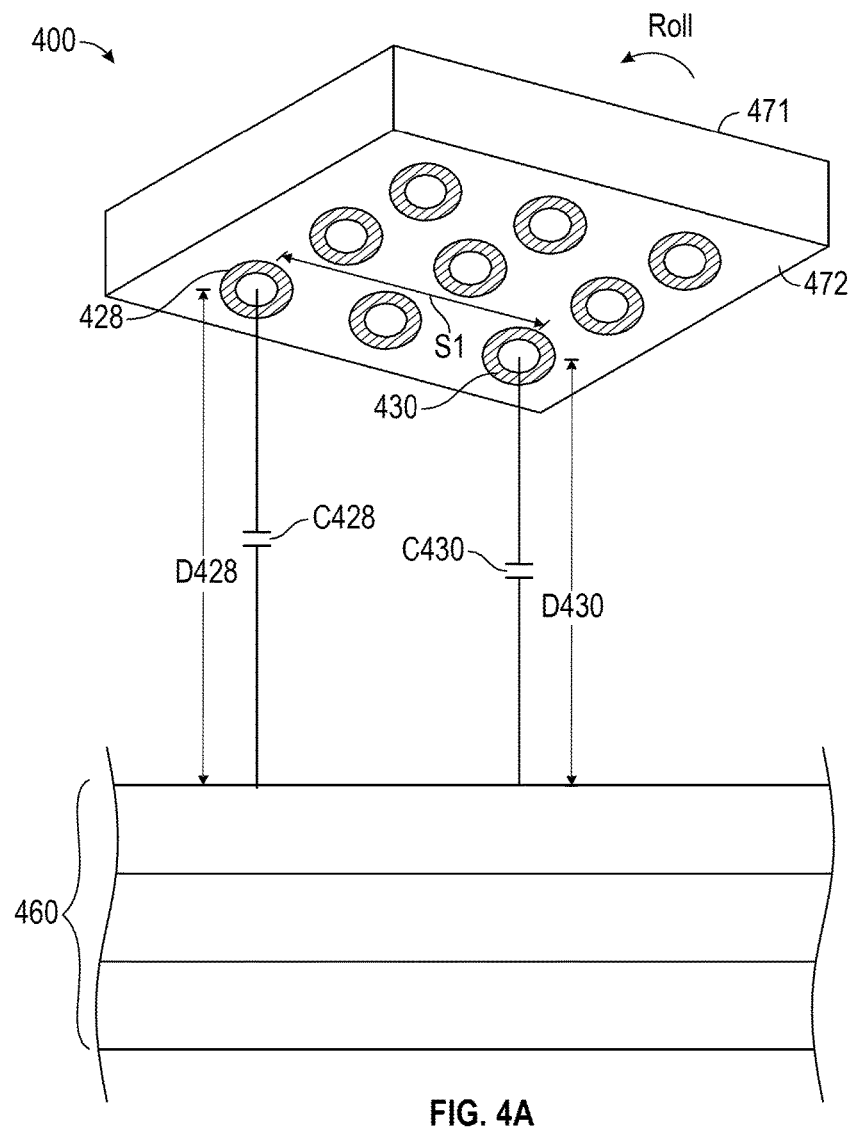
FIGS. 4A-4B illustrate an exemplary determination of the rotational angles of an exemplary portable electronic device with electrodes located on the underside.
Figure 4B:
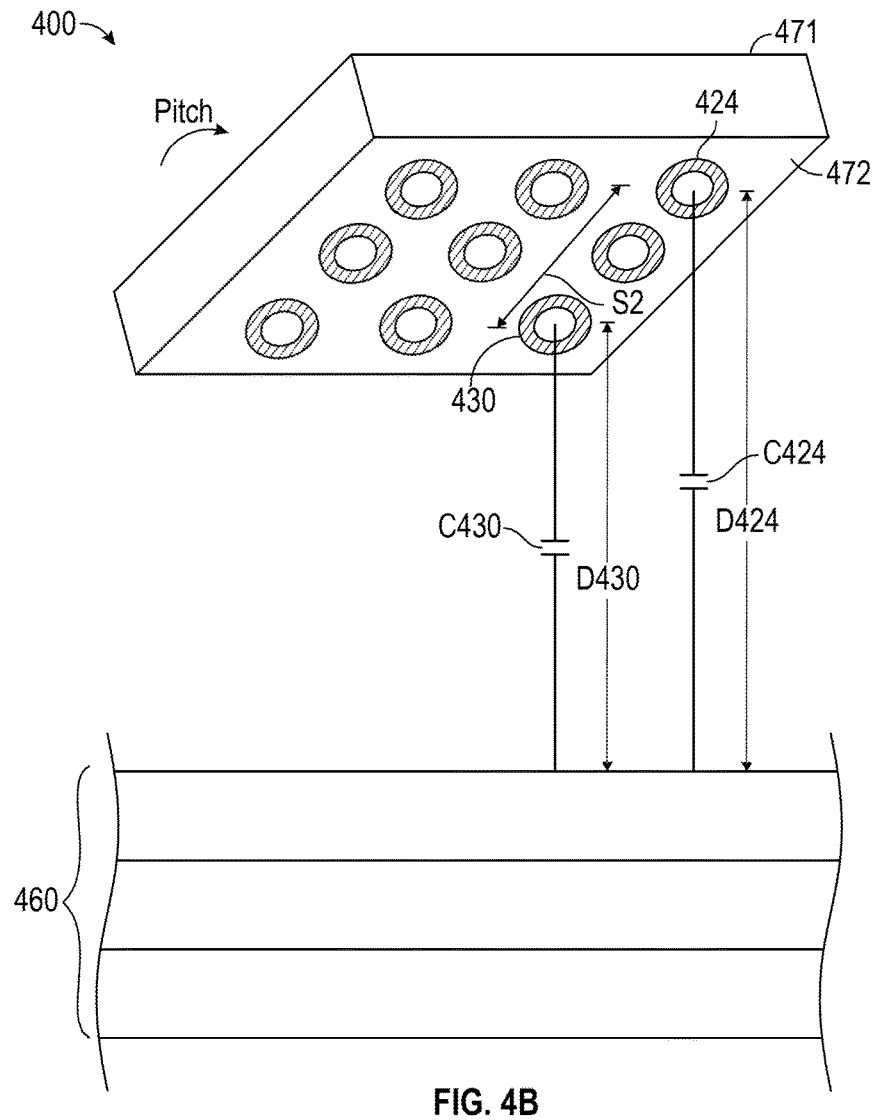

Based on the distance calculated by the electrodes, rotational angles of the device relative to the user's body part can also be calculated. FIGS. 4A-4B illustrate an exemplary determination of the rotational angles of an exemplary portable electronic device with electrodes located on the underside. Device 400 can be attached to, resting on, or touching a part of the user such that the underside 472 of the device faces a body part 460 of the user, and the top surface 471 can be located in the user's line of sight. Device 400 can include electrodes 428, 430, and 424 located on the underside 472 of the device. Electrode 428 can be located a distance $d_{428}$ from the body part 460, electrode 430 can be located a distance $D_{430}$ from the body part, and electrode 424 can be located a distance $d_{424}$ from the body part. Due to the conductive nature of the human skin, capacitances $C_{428}$, $C_{430}$, and $C_{424}$ can form between the electrodes 428, 430, and 424, and body part 460. The distances $D_{428}$, $D_{430}$, and $D_{424}$ can be calculated based on the capacitance values, as discussed above. From the calculated distances, the pitch and roll of the device 400 can be used to quantify the three-dimensional rotation of the device 400 relative to the user's body part 460. Electrodes 428 and 430 can be separated by a distance of S1 from each other, and electrodes 430 and 424 can be separated by a distance S2. The roll can be the amount of rotation about the longitudinal axis, as shown in FIG. 4A, and can be expressed as:

$$\text{roll} = \sin^{-1} \frac{D_{428} - D_{430}}{S1}$$

The pitch can be the amount of rotation about the lateral axis, as shown in FIG. 4B, and can be expressed as:

$$\text{pitch} = \sin^{-1} \frac{D_{424} - D_{430}}{S2}$$

In some examples, multiple pitch values and roll values between different pairs of electrodes can be calculated. The device can average the multiple values and/or construct a contour map. It should be understood that although FIGS. 3A-3C and 4A-4B and their corresponding text above disclose capacitive electrodes for determining distances between the device and a user body part. In some examples, the underside may or may not include other sensors, such as light sensors, or emitters. In other examples of the disclosure other circuitry for detecting distances can be used, such as optical proximity sensors. In other examples, the same optical sensors used to estimate characteristics of the user (see, e.g., FIG. 2) can be time multiplexed to determine distances, pitch and roll for subsequent compensation calculations.

Figure 5A:
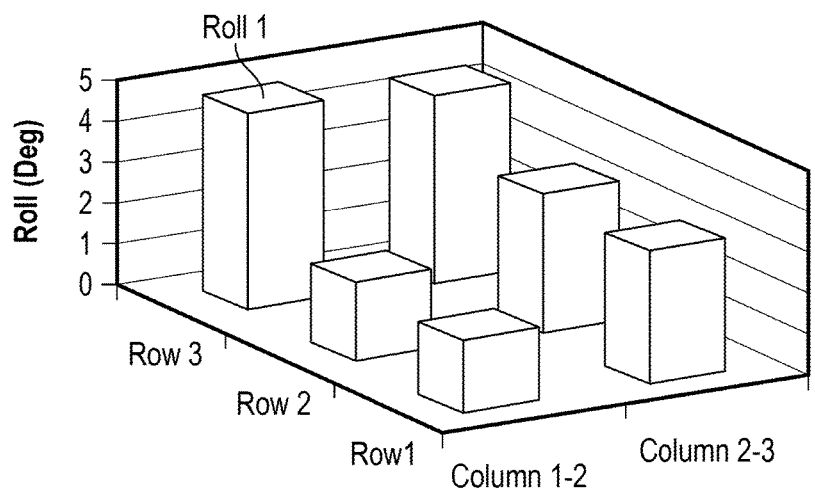
FIGS. 5A-5F illustrate rotational angles calculated by an exemplary portable electronic device attached to a user's wrist with nine electrodes located on the underside of the device.
Figure 5B:
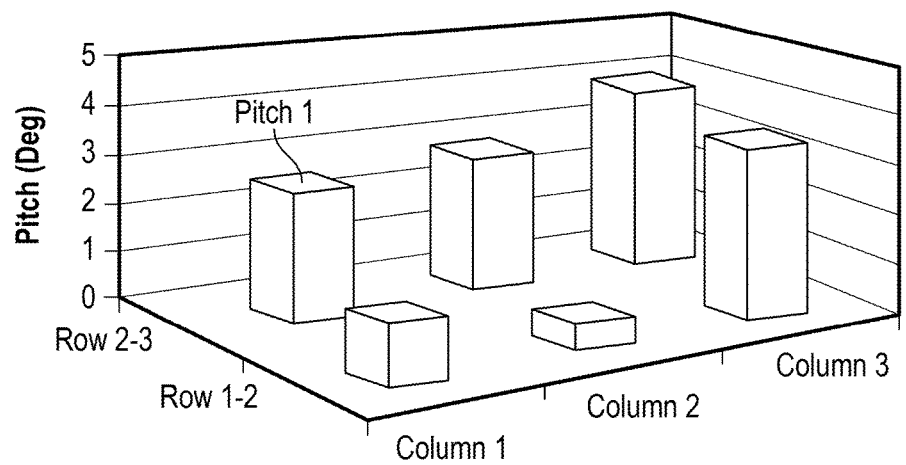
Figure 5C:
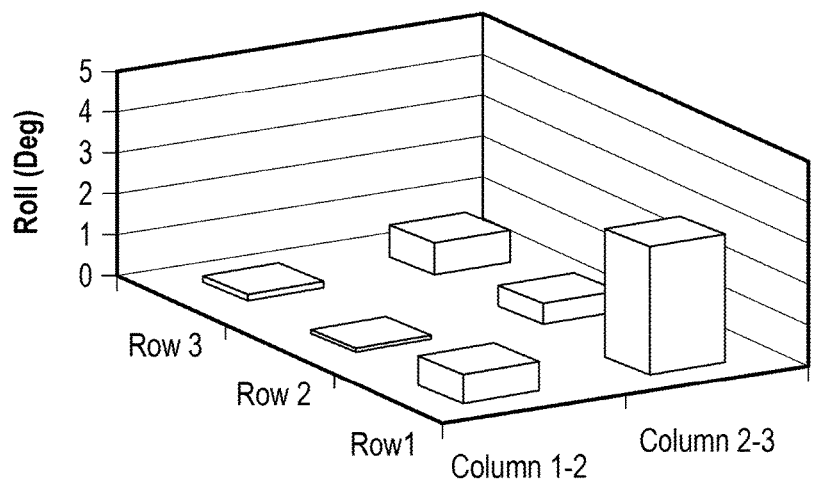
Figure 5D:
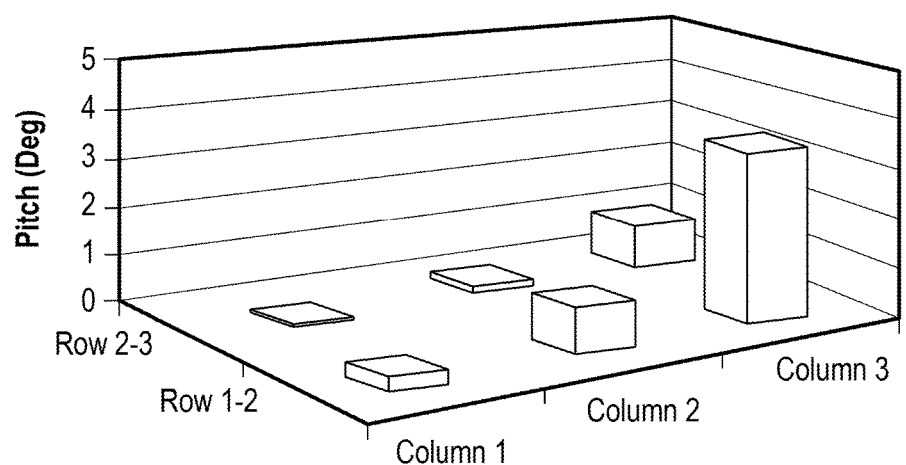
Figure 5E:
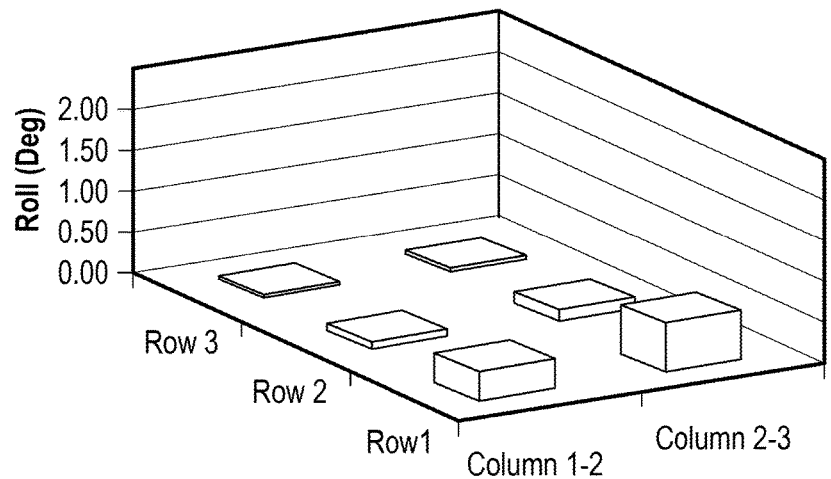
Figure 5F:
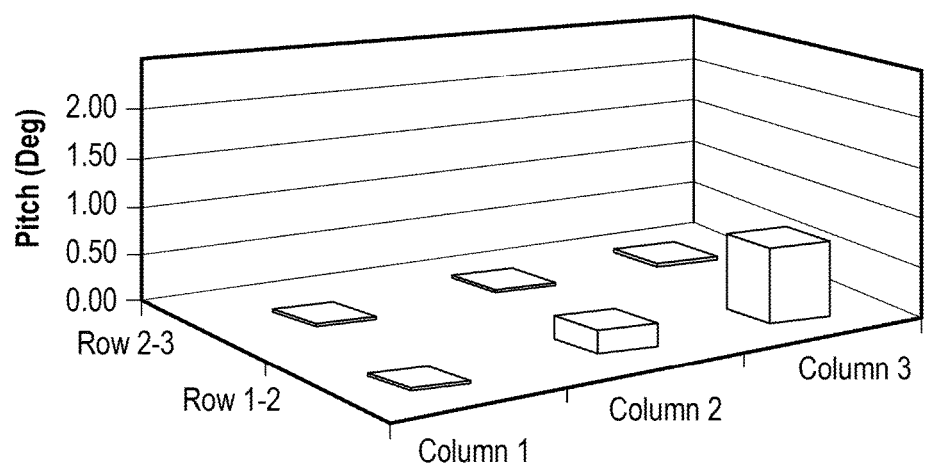

FIGS. 5A-5F illustrate rotational angles calculated by an exemplary portable electronic device attached to a user's wrist with nine electrodes located on the underside of the device. FIGS. 5A-5B illustrate calculated pitch and roll angles when the user is jogging. The rows and columns can be designated as shown in FIG. 3B. Using the capacitance values measured and calculated distances from the nine electrodes, six roll and six pitch values or angles can be calculated. For example, Roll 1 represents the roll calculated from electrodes 328 and 329 of FIG. 3B, and Pitch 1 represents the pitch calculated from electrodes 325 and 326 of FIG. 3B. FIGS. 5C-5D illustrate calculated pitch and roll angles when the user is clenching their fist, and FIGS. 5E-5F illustrate calculated pitch and roll angles when the user is flexing their fingers. Based on one or more of the pitch, roll, and contour map, the device can determine or at least predict physical activities being performed by a user. Additionally, the device can determine or at least estimate the intensity of the physical activities based on the magnitude of the calculated roll and pitch values. In some examples, the device can compute the calculated rotational angles in conjunction with the outputs from other device components, such as the light emitters and optical sensors.

Figure 6:
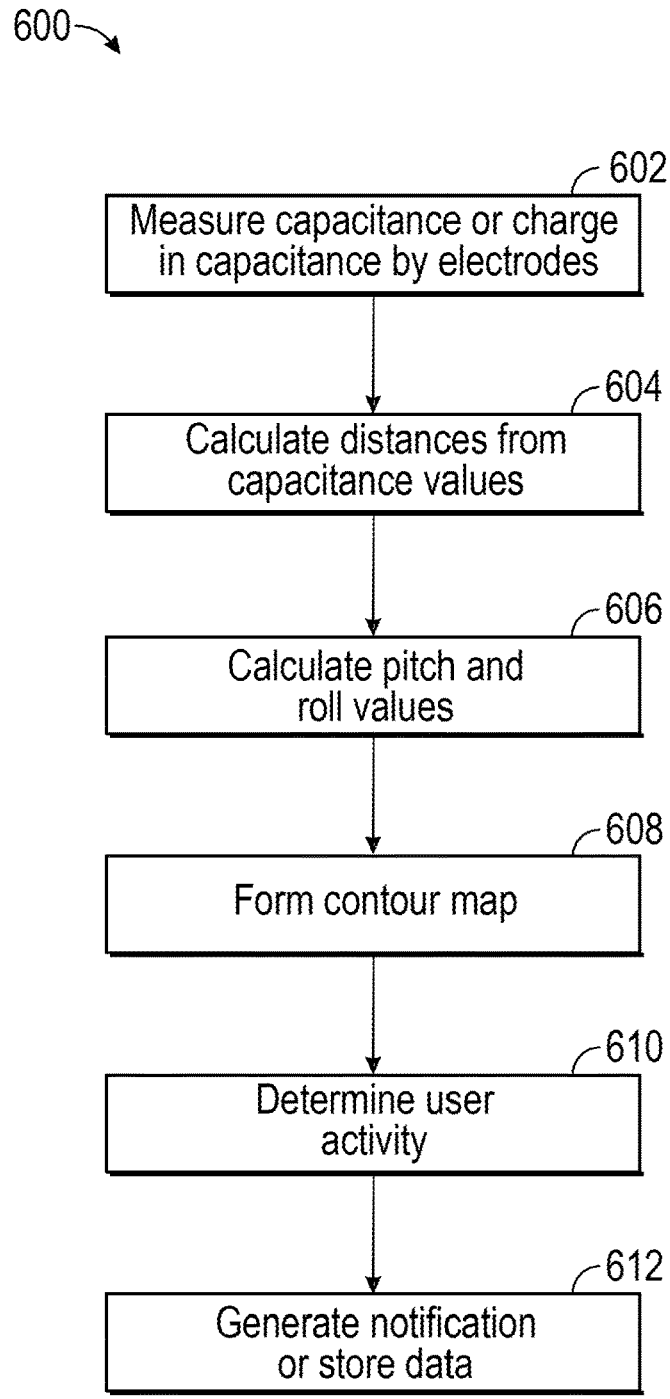
FIG. 6 illustrates a flow chart of an exemplary process flow for calculating distances and rotational angles of an exemplary portable electronic device relative to a user.

FIG. 6 illustrates a flow chart of an exemplary process flow for calculating the distance and rotational angles of an exemplary portable electronic device relative to a user. Process 600 can begin at 602 where the capacitance or change in capacitance can be measured at one or more electrodes. At 604, the distances from the electrodes to the body part can be calculated based on the measured capacitance values. At 606, one or more pitch and roll values can be calculated from the calculated distances. At 608, a contour map can be generated. At 610, the device can optionally determine or at least estimate the user's physical activity and intensity based on the pitch and roll values and the contour map. At 612, the device can optionally generate a notification to the user or store the information for future purposes or historical tracking. For example, for a user undergoing physical therapy for a tendonitis issue, the device can notify a user of excessive wrist movement based on one more of the distance, pitch and roll information that exceeds magnitude and/or duration thresholds. The device can track the user's movement over the course of a certain timeframe, and a doctor can use the historically tracked information for therapy purposes. In another example, the device can utilize one or more of the distance, pitch and roll information to detect low intensity trembling or shaking and correlate the movement with excessive stress. In response to this detected movement, the device can notify the user to relax or play relaxing music to calm the user down.

In some examples, the pitch and roll can be used to enhance the user's experience by adjusting properties of other components or activating other features in the portable electronic device. For example, a determination of the user jogging intensely can activate a timer and the device can automatically track and store the user's speed or running pace. In other examples, the device can determine when the user is exhibiting minimal movement and can turn off components that can consume a significant amount of power, such as the display.

Figure 7A:
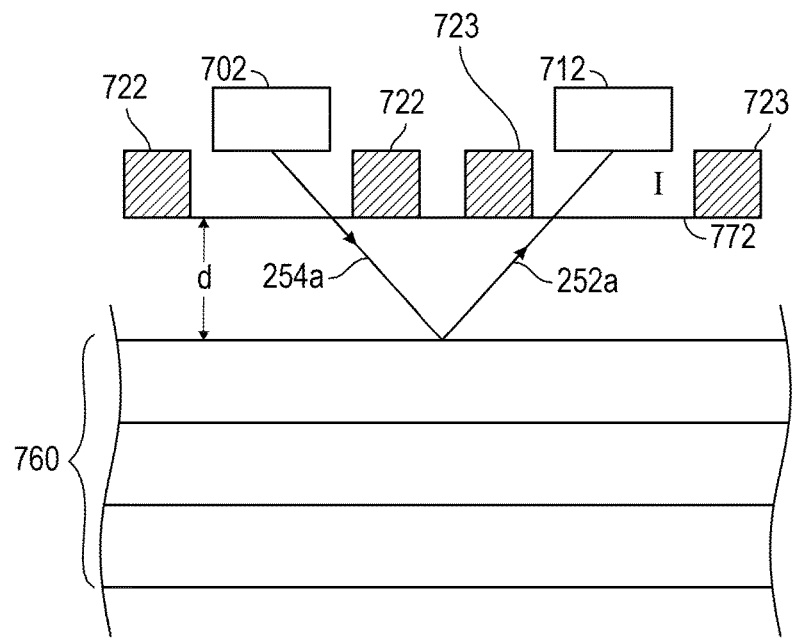
FIGS. 7A-7B illustrate a cross-sectional view of the underside of an exemplary portable electronic device.
Figure 7B:
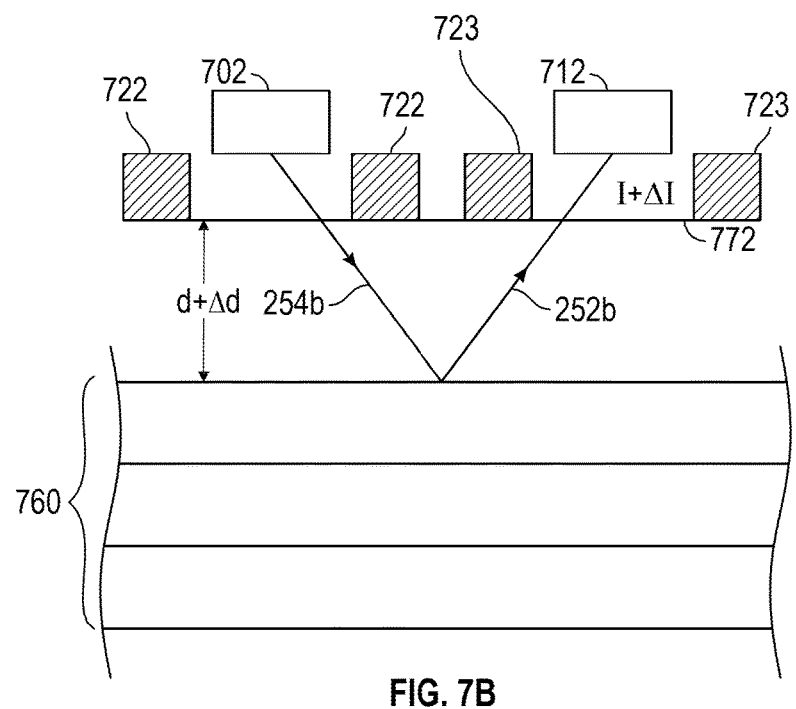

In addition to utilizing the calculated distances between the user and the electrodes for determining or estimating a physical activity of the user, the portable electronic device can also use the calculated distance for other purposes, such as cancellation of optical artifacts introduced due to user movement. FIGS. 7A-7B illustrate a cross-sectional view of the underside of an exemplary portable electronic device. The underside 772 of the device can include light emitter 702, optical sensor 712, and electrodes 722 and 723 facing the user's body part 760. FIG. 7A illustrates the underside 772 located a first distance d from the body part 760. FIG. 7B illustrates the underside 772 located a second distance d+Δd when the gap between the device and body part changes as a result of, for example, the user moving. A light emitter 702 can emit light 254a towards the user's body part 760. A portion of the light can be absorbed by the skin, flesh, blood, and/or other parts of the user's body, and an additional portion of light can be reflected back to the optical sensor as reflected light 252a. If the user moves, the distance between the underside of the device and the user's body part can change by a distance Δd, as shown in FIG. 7B. Due to the change in distance Δd caused by user movement, the light 254b emitted from the light emitter 702 may have to travel a longer distance (compared to light 254a of FIG. 7A) before reaching the body part 760. Similarly, reflected light 252b may have to travel a longer distance (compared to reflected light 252a of FIG. 7A) before reaching the optical sensor 712. As a result, the intensity of the light detected by the optical sensor 712 may also change by an amount ΔI_PD. The device can be unaware of a change in distance Δd, and the device can mistakenly believe that the change in light sensed by the optical sensor was due to a change in one or more characteristics of the user. However, with electrodes 722 and 723, the distance change Δd can be calculated, and the change in intensity of light AI due to the distance change can be used to compensate for optical artifacts. Accounting for the change in detected light due to a change in distance between the user and the underside of the device, the photodiode current I_PD value can be expressed as:

$$I\_PD \propto d \times m$$
$$m = \frac{\Delta I\_PD}{\Delta d}$$

In some examples, the device may move closer in response to user movement, and the distance change Δd and intensity change ΔI_PD can be negative in value. In some examples, the device may move further away in response to user movement, and the distance change Δd and intensity change ΔI_PD can be positive in value. In some examples, the compensation can be applied when the distance change Δd or the intensity change ΔI_PD exceeds a predetermined value.

Figure 8:
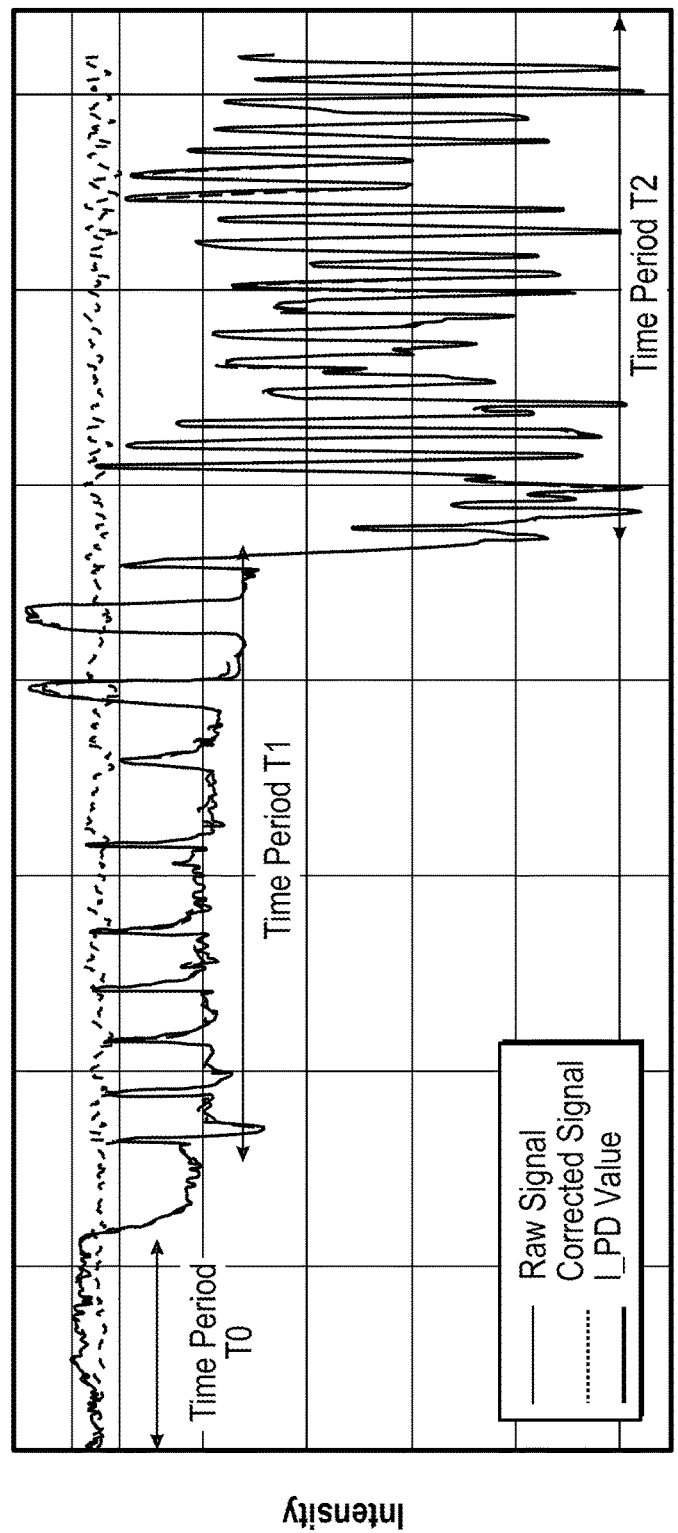
FIG. 8 illustrates an exemplary compensation of a user's heart rate due to a change in physical activity according to various examples of the disclosure.

Determining or estimating the user activity can be particularly useful not only for generating notifications and historical tracking, but also for other device measurements where a user activity can introduce optical artifacts. For example, optical artifacts can comprise a large percentage of the signal read from the optical sensors located on the underside of the device. Compensation can thereby prevent or reduce erroneous readings. FIG. 8 illustrates an exemplary compensation of a user's heart rate due to a change in physical activity according to various examples of the disclosure. A portable electronic device including light emitters, optical sensors, and electrodes disposed on the underside of the device can be attached to the user's wrist. The light emitters and optical sensors can produce a raw signal that can be used to measure the heart rate of the user based on light passing through the user's skin and reflecting a portion of the light to the optical sensors. The electrodes can be used to determine the user's physical activity, distance between the device and the user's body part, pitch, roll, etc. The raw signal can be the signal I+ΔI_PD measured at the optical sensors for determining, for example, the user's heart rate. The computed I_PD value can be the estimated photocurrent signal due to user's physical activity. The I_PD value can be applied to the raw signal, resulting in the corrected signal. The corrected signal can be the signal used for determining one or more characteristics of the user. In some examples, the I_PD value can be applied to the raw signal using at least one of addition, subtraction, multiplication, and division.

As shown in FIG. 8, during a time period T0, the user can be performing minimal movement. As a result, there are no optical artifacts introduced into the measured raw signal. During a time period T1, the user can flex their index finger, while maintaining a constant heart rate. Due to a movement of the user's index finger, the raw signal measured by the optical sensors can change significantly. The change in raw signal can be, however, not due to a change in the user's heart rate. If the device were unaware of the user flexing their index finger, the device could mistakenly interpret the change in the raw signal as a significant change in the user's heart rate. To reduce optical artifacts and avoid mistaken interpretations, electrodes can be used to estimate the I_PD value and adjust the raw signal based on the I_PD value. The corrected signal can result from the raw signal adjusted based on the I_PD value, and can be generated by subtracting, adding, multiplying, dividing, or performing any one of a number of mathematical operations on the raw signal and I_PD value. The device can use the corrected signal for a more accurate determination of the user's heart rate. Similarly, during a time period T2, the user can flex all of their fingers without a change in heart rate. Flexing all of the user's fingers can lead to a dramatic change in the raw signal. The electrodes can be used to measure the I_PD value, and the I_PD value can be applied to the raw signal to result in the corrected signal. The device can attribute the changes in the raw signal to the user's physical activity, instead of changes in one or more other characteristics of the user.

Figure 9:
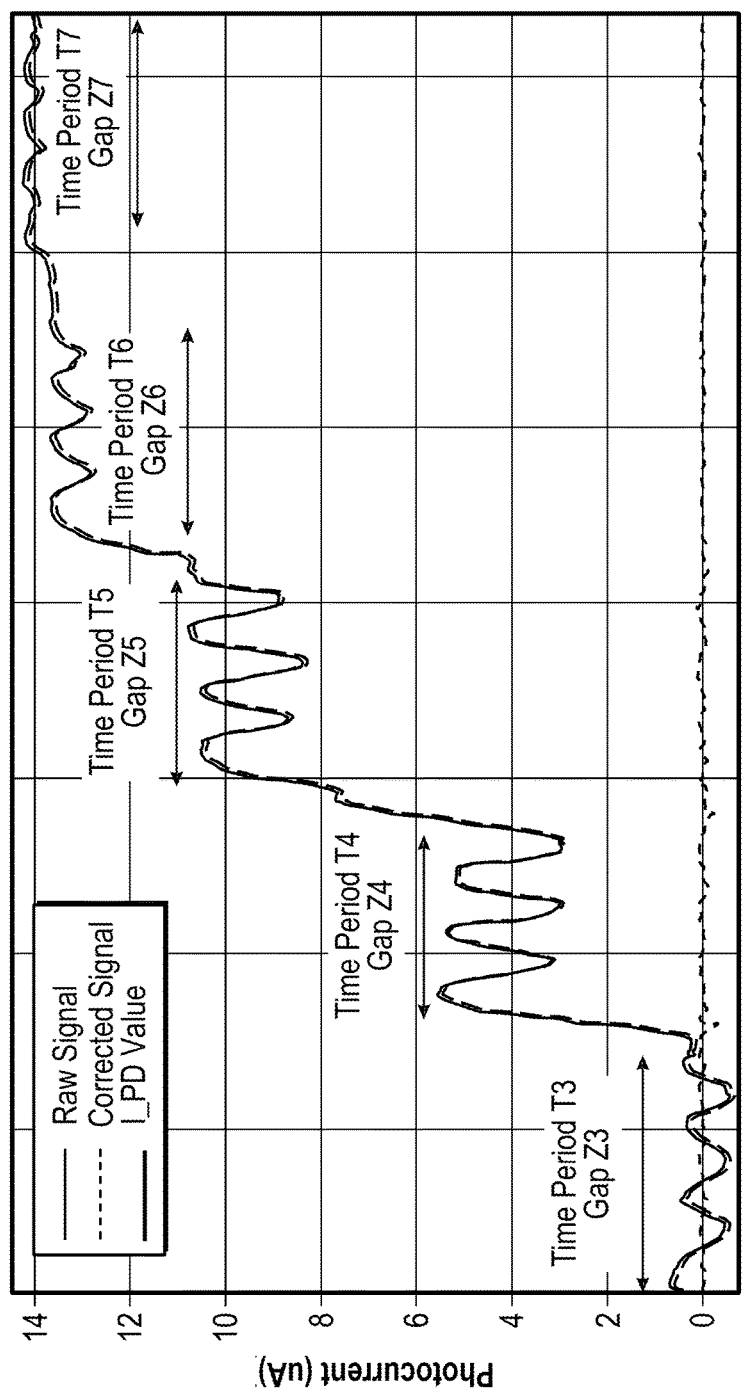
FIG. 9 illustrates an exemplary compensation of a user's heart rate due to a change in distance between a portable electronic device and the user's body part according to various examples of the disclosure.

FIG. 9 illustrates an exemplary compensation of a user's heart rate due to a change in distance between a portable electronic device and the user's body part according to various examples of the disclosure. The device can compensate for a change in gap between the device and the user's body part. The I_PD value can be calculated due to a change in distance between the device and user's body part, and the raw signal can be adjusted based on the I_PD value. As shown in FIG. 9, the device can be measuring a user's heart rate by utilizing a light emitter and sensor pair. The light emitter can be located on the underside of the device, and directing light towards the user's skin. A portion of the light can be reflected back to a light sensor located near the light emitter on the underside of the device. Electrodes can be also located on the underside of the device in close proximity to the sensor. The optical sensors can detect a photocurrent, or the raw signal. Measurements from the optical sensors can be taken during five time periods, for example: T3, T4, T5, T6, and T7. During the time periods of the present example, the user was inactive and had minimal change in heart rate. The device was offset from the user's body part by five different gaps: Z3, Z4, Z5, Z6, and Z7. The changes in gap caused changes in photocurrent detected by the optical sensors that could be erroneously interpreted by the device as changes in heart rate. However, according to examples of the disclosure, electrodes can be used to measure the changes in capacitance due to the changes in gap. Based on the measured changes in capacitance, the I_PD value, or the estimated photocurrent due to changes in gap, can be calculated. The I_PD value can then be applied to the raw signal to produce the corrected signal. The corrected signal can compensate for any optical artifacts in the raw signal, and can lead to a more accurate determination of the one or more characteristics of the user, such as their heart rate. In some examples, the raw signal can be adjusted based on the I_PD value using at least one of addition, subtraction, multiplication, and division. While FIG. 9 illustrates a user's heart rate, the examples of the disclosure can include, but are not limited to other characteristics of the user.

Figure 10:
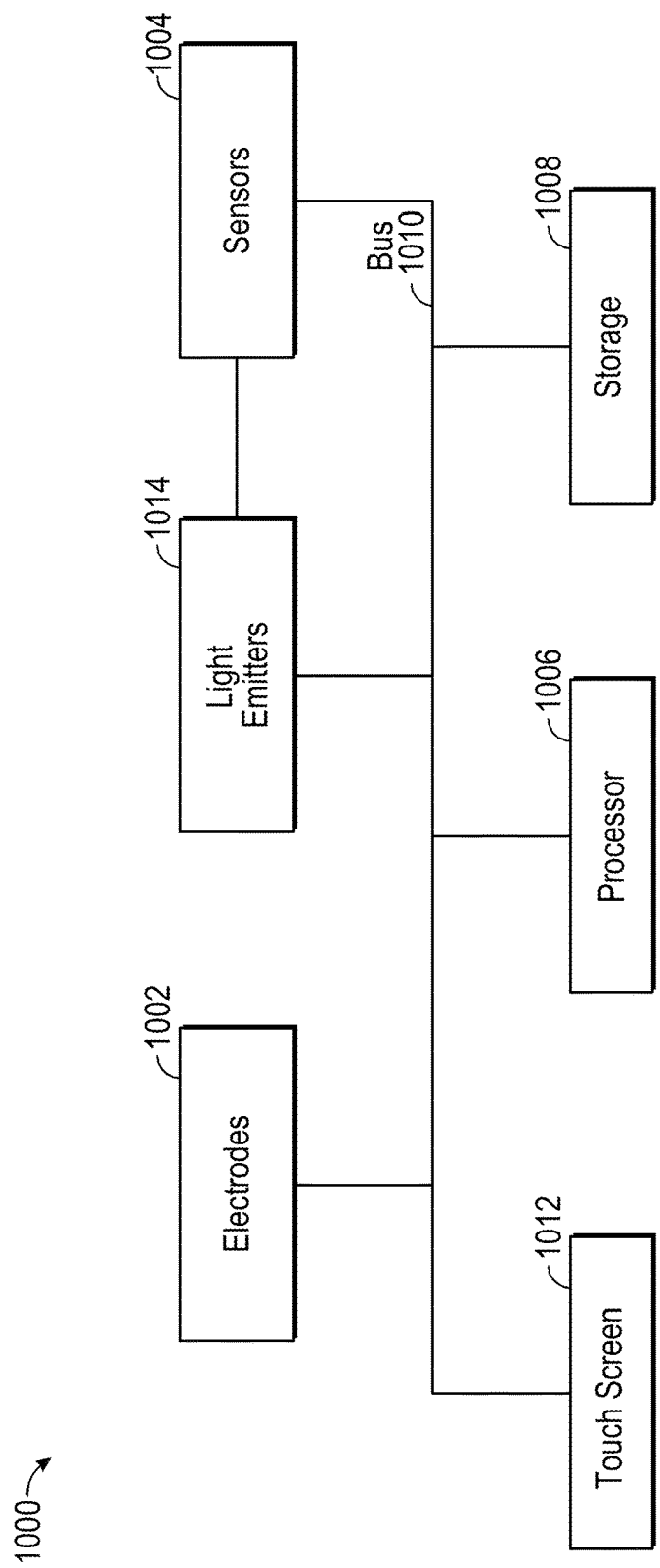
FIG. 10 illustrates an exemplary system 1000 according to examples of the disclosure.

FIG. 10 illustrates an exemplary system 1000 according to examples of the disclosure. System 1000 can include touch screen 1012, one or more processors 1006, and storage 1008. System 1000 can also include one or more electrodes 1002 for determining the proximity and tilt of the device relative to the user body part, and other sensors 1004, such as those described above. Other sensors 1004 can also include other sources of information, as described above. All of the above can be communicatively coupled via bus 1010.

Electrodes 1002 can output electrode signals to processor 1006 for processing via bus 1010. Other sensors 1004, if included in system 1000, can also output sensor outputs to processor 1006 for processing via bus 1010. Touch screen 1012 can be the touch screen on the device according to examples of the disclosure, although non-touch screen examples, such as touchpad, also fall within the scope of the disclosure. Storage 1008 can be any non-transitory computer-readable storage medium, and can store, for example, history and/or pattern data relating to measurements from the electrodes 1002 and other sensors 1004. Storage 1008 can also store instructions that can cause processor 1006 to perform distance and rotational angle calculations, determine a user physical activity, or compensate for optical artifacts in the outputs of sensors 1004. Processor 1006 can generate notifications or monitor the user movement, as described in the disclosure.

Note that one or more of the functions described above can be performed, for example, by firmware stored in memory (e.g. storage 1008) and executed by processor 1006. The firmware can also be stored and/or transported within any non-transitory computer-readable storage medium (not including signals) for use by or in connection with an instruction execution system, apparatus, or device, such as a computer-based system, processor-containing system, or other system that can fetch the instructions from an instruction execution system, apparatus, or device and execute the instructions. In the context of this document, a "non-transitory computer-readable storage medium" can be any medium (excluding a signal) that can contain or store the program for use by or in connection with the instruction execution system, apparatus, or device. The non-transitory computer readable storage medium can include, but is not limited to, an electronic, magnetic, optical, electromagnetic, infrared, or semiconductor system, apparatus, or device, a portable computer diskette (magnetic), a random access memory (RAM)(magnetic), a read-only memory (ROM) (magnetic), an erasable programmable read-only memory (EPROM)(magnetic), a portable optical disc such as a CD, CD-R, CD-RW, DVD, DVD-R, or DVD-RW, or flash memory such as compact flash cards, secured digital cards, USB memory devices, memory sticks, and the like.

In some examples, a device is disclosed. The device may comprise: one or more electrodes located on a surface of the device; sensing circuitry coupled to the one or more electrodes and configured to generate sense signals indicative of one or more distances between the one or more electrodes and a proximate object; and logic coupled to the one or more electrodes, the logic configured to calculate the one or more distances. Additionally or alternatively to one or more the examples described above, the one or more electrodes are configured such that the one or more electrodes are electrically isolated from one another and occupy substantially a full area of the surface of the device. Additionally or alternatively to one or more the examples described above, a cover layer disposed on the surface of the device, the device further comprises: a cover layer, wherein the cover layer is configured to allow capacitive coupling from the one or more electrodes to the proximate object. Additionally or alternatively to one or more the examples described above, the device further comprises: a shield, wherein the shield is disposed around at least one of the one or more electrodes and is configured to eliminate or reduce external interference. Additionally or alternatively to one or more the examples described above, the device further comprises: an insulating layer; and a shield disposed over the insulating layer, wherein the shield is configured to eliminate or reduce internal interference. Additionally or alternatively to one or more the examples described above, the device further comprises: a drive circuitry configured to drive at least one of the electrodes and form an electric field coupled to another electrode, wherein the sense circuitry senses a change in capacitance. Additionally or alternatively to one or more the examples described above, the logic is further configured to calculate one or more angles based on the calculated one or more distances and a physical activity is estimated from the calculated one or more angles. Additionally or alternatively to one or more the examples described above, the physical activity includes at least one of wrist movement, finger movement, trembling, and jogging. Additionally or alternatively to one or more the examples described above, the device further comprises: a memory configured to store at least one of the sensed signals, the calculated one or more distances, and the physical activity. Additionally or alternatively to one or more the examples described above, the device further comprises: one or more sensors configured to generate first signals, wherein the logic further comprises adjusting the first signals based on the sensed signals. Additionally or alternatively to one or more the examples described above, the logic applies the sensed signals to the first signals by performing at least one of an addition, subtraction, multiplication, and division. Additionally or alternatively to one or more the examples described above, the device further comprises: one or more light emitters configured to generate light directed at the proximate object, wherein the one or more sensors are configured to detect the light generated from the one or more light emitters and passing through or reflected from the proximate object. Additionally or alternatively to one or more the examples described above, the one or more sensors and the one or more light emitters are located on the surface of the device. Additionally or alternatively to one or more the examples described above, the device further comprises: one or more filters coupled to the one or more sensors, each filter configured to pass through one or more wavelengths of light.

In some examples, a method of a device including one or more electrodes facing a proximate object is disclosed. The method may comprise: detecting one or more capacitances coupled to the proximate object from the one or more electrodes; generating sense signals indicative of one or more distances between the one or more electrodes and the proximate object; and calculating the one or more distances based on the sense signals. Additionally or alternatively to one or more the examples described above, the method further comprises: calculating one or more angles based on the calculated one or more distances; and estimating a physical activity from the calculated one or more angles.

Additionally or alternatively to one or more the examples described above, the method further comprises: storing at least one of the sensed signals, one or more distances, one or more angles, and the physical activity. Additionally or alternatively to one or more the examples described above, the method further comprises: changing an operating state at least one of a display or a touch panel of the device based on the estimated physical activity. Additionally or alternatively to one or more the examples described above, the method further comprises: driving one or more electrodes to form an electric field with another electrode. Additionally or alternatively to one or more the examples described above, the method further comprises: generating light directed at the proximate object; generating first signals from the light directed at the proximate object and passing through or reflected from the proximate object; and adjusting the first signals based on the sensed signals. Additionally or alternatively to one or more the examples described above, the method further comprises: filtering the light passing through or reflected from the proximate object.

In some examples, a non-transitory computer readable storage medium is disclosed. The computer readable medium containing instructions that, when executed, perform a method of an electronic device including one or more electrodes, the method comprising: detecting one or more capacitances coupled to the proximate object from the one or more electrodes; generating sense signals indicative of one or more distances between the one or more electrodes and the proximate object; and calculating the one or more distances based on the sense signals. Additionally or alternatively to one or more the examples described above, the method further comprises: calculating one or more angles based on the calculated one or more distances. Additionally or alternatively to one or more the examples described above, the method further comprising: estimating a physical activity from the calculated one or more angles; and changing an operating state of at least one of a display or a touch panel of the device based on the estimated physical activity. Additionally or alternatively to one or more the examples described above, the method further comprises: generating light directed at the proximate object; generating first signals from the light directed at the proximate object and passing through or reflected from the proximate object; and adjusting the first signals based on the sensed signals.

While various examples have been described above, it should be understood that they have been presented by way of example only, and not by way of limitation. Although examples have been fully described with reference to the accompanying drawings, the various diagrams may depict an example architecture or other configuration for this disclosure, which is done to aid in the understanding of the features and functionality that can be included in the disclosure. The disclosure is not restricted to the illustrated exemplary architectures or configurations, but can be implemented using a variety of alternative architectures and configurations. Additionally, although the disclosure is described above in terms of various examples and implementations, it should be understood that the various features and functionality described in one or more of the examples are not limited in their applicability to the particular example with which they are described. They instead can be applied alone or in some combination, to one or more of the other examples of the disclosure, whether or not such examples are described, and whether or not such features are presented as being part of a described example. Thus, the breadth and scope of the present disclosure should not be limited by any of the above-described examples.

What is claimed is:

1. A device comprising:
a touch panel including a touch screen located on a first surface of the device;
one or more electrodes located on a second surface of the device, the second surface opposite the first surface;
sensing circuitry coupled to the one or more electrodes and configured to generate sense signals indicative of one or more distances between the one or more electrodes and a proximate object; and
logic coupled to the one or more electrodes, the logic calculates the one or more distances.

2. The device of claim 1, wherein the one or more electrodes are electrically isolated from one another and occupy substantially a full area of the second surface of the device.

3. The device of claim 1, further comprising:
a cover layer disposed on the second surface of the device, wherein the cover layer is configured to allows capacitive coupling from the one or more electrodes to the proximate object.

4. The device of claim 1, further comprising:
an insulating layer disposed over the one or more electrodes; and
a shield disposed over the insulating layer and opposite the second surface, wherein the shield eliminates or reduces internal interference.

5. The device of claim 1, further comprising:
a drive circuitry that drives at least one of the one or more electrodes and forms an electric field coupled to at least a second of the one or more electrodes, wherein the sense circuitry generates sense signals including a change in capacitance between the at least one of the one or more electrodes and the another electrode.

6. The device of claim 1, wherein the logic further:
calculates one or more angles based on the calculated one or more distances, and
estimates a physical activity from the calculated one or more angles.

7. The device of claim 1, further comprising:
one or more sensors that generates first signals, wherein the logic further comprises adjusting the first signals based on the sensed signals.

8. The device of claim 7, further comprising:
one or more light emitters that generate light directed at the proximate object, wherein the one or more sensors detect the light generated from the one or more light emitters and passing through or reflected from the proximate object.

9. The device of claim 8, wherein the one or more sensors and the one or more light emitters are located on the second surface of the device.

10. The device of claim 6, the device further comprising:
a display, wherein the device is capable of changing an operating state of at least one of a display or the touch panel based on the estimated physical activity.

11. The device of claim 1, wherein the logic further:
calculates one or more differences between at least two of the calculated one or more distances; and
determines a first rotation of the device about a first axis based on the calculated one or more differences.

* * * * *